(12) United States Patent
Gately

(10) Patent No.: US 6,410,767 B2
(45) Date of Patent: Jun. 25, 2002

(54) SILYLATED AND N-SILYLATED COMPOUND SYNTHESIS

(75) Inventor: Daniel A. Gately, Berthoud, CO (US)

(73) Assignee: Boulder Scientific Co., Mead, CO (US)

( * ) Notice: Subject to any disclaimer, the term of this patent is extended or adjusted under 35 U.S.C. 154(b) by 7 days.

(21) Appl. No.: 09/816,496

(22) Filed: Mar. 26, 2001

Related U.S. Application Data

(62) Division of application No. 09/016,641, filed on Jan. 30, 1998.

(51) Int. Cl.$^7$ ................................................ C07F 7/10
(52) U.S. Cl. ...................................... 556/410; 556/428
(58) Field of Search ................................ 556/410, 427, 556/428

(56) References Cited

PUBLICATIONS

CA:125:59306 abs of Z Naturforsch B: Chem. Sci 51(5) pp. 703–707 by Uhlig 1996.*
CA:120:298681 abs of J Organomet. Chem. by Uhlig 467(1), pp. 31–35 1994.*

* cited by examiner

*Primary Examiner*—Jean F. Vollano
(74) *Attorney, Agent, or Firm*—Edward S. Irons

(57) ABSTRACT

Synthesis of N-silylated mono(cyclopentadienyl) ligands and similar indenyl ligands utilizing the novel silanes is described.

2 Claims, No Drawings

SILYLATED AND N-SILYLATED COMPOUND SYNTHESIS

This application is a division of U.S. application Ser. No. 09/016,641 filed Jan. 30, 1998.

FIELD OF INVENTION

This invention relates to certain novel silanes and to the synthesis of silylated and N-silylated organic compounds therewith.

BACKGROUND OF THE INVENTION

Typical procedures for the synthesis of silylated and N-silylated bis and mono(cyclopentadienyl) and indenyl ligands involve the addition of $Cl_2Si(CH_3)_2$ during synthesis of monocyclopentadienyl compounds to the lithiated ligand precursor. These procedures are not cost effective due to a requirement for excess $Cl_2Si(CH_3)_2$, the production of undesirable by-products, and a consequent need for expensive purification procedures.

DEFINITIONS

In this specification, the following expressions have the meanings set forth:

1. MsO means $CH_3O_3S$ or

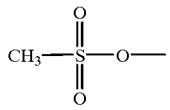

2. MsOH means $CH_4O_3S$ or

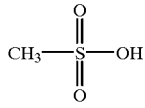

3. TfO means $CF_3O_3S$ or

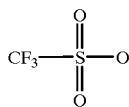

4. TfOH means $CHF_3O_3S$ or

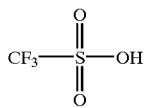

5. Monocyclopentadienyl ligand means any ligand having the formulae $C_5H_xR_y$, wherein:

X=0-5
y=0-5
R=any alkyl or aromatic group or combination thereof, and H or R can occupy any one or more of the positions 1 to 5 of the formula

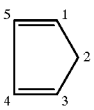

For example, R may be an alkyl group having one to eight carbon atoms including but not limited to methyl, ethyl, propyl, isopropyl, butyl, tertbutyl, hexyl or octyl. Methyl is the preferred alkyl group. R, when an aromatic group, may be phenyl, xylyl, mesityl, naphthyl or fluorenyl.

6. Silylated monocyclopentadienyl ligand means any ligand having the formula $(R_3Si)_zC_5H_xR_y$, wherein $C_5H_xR_y$ is as defined in definition 5, Z=1-5 and R and $R_y$ are identical or different alkyl or aromatic groups.

7. N-silylated monocyclopentadienyl ligand means any ligand having the formula $RNH(SiR_2)C_5H_xR_y$, wherein $C_5H_xR_y$ is as defined in definition 5, and R and $R_y$ are identical or different alkyl or aromatic groups.

8. Silylated biscyclopentadienyl ligand means any ligand having the formula $(C_5H_xR_y)_2SiR_2$, wherein $C_5H_xR_y$ and $R_y$ are as defined by definitions 6 and 7.

9. Silylated monoindenyl ligand means any ligand having the formula $(R_3Si)(C_9H_xR_y)$ wherein X=0-7
y=0-7

H or R can occupy any positions 1 to 7 and $R_3Si$ can occupy only position 3 of the formula

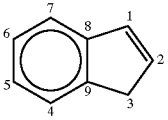

wherein R and $R_y$ are as defined by definitions 6 and 7.

10. N-silylated monoindenyl ligand means any ligand having the formula $RNH(SiR_2)C_9H_xR_y$, wherein R and $R_y$ are as defined by definitions 6 and 7. $(C_9H_xR_y)$ is as defined in definition 9 and wherein X=0-7 and y=0-7.

11. Silylated bisindenyl ligand means any ligand having the formula $(R_2Si)C_9H_xR_y$ wherein R and $R_y$ are as defined in definitions 6 and 7; X=0-7 and y=0-7.

SUMMARY OF THE INVENTION

One aspect of the invention includes novel silanes having the Formula (I):

$$(CX_3SO_3)_2SiR_2 \qquad (I)$$

or the Formula (II):

in which X is H or F, each R in formula (I) may be the same or a different alkyl or aromatic group as defined by definition 5 with the proviso that when X is F in formula (I), R is not methyl, and $R^1$ is an alkyl or aromatic group which may be the same or different from R.

Another aspect of the invention is a method for the synthesis of silylated and N-silylated compounds having the Formula (III)

$$Y_2Si(R)_2 \qquad (III)$$

or the Formula (IV)

(IV)

in which Y is any organic group and in which R and $R^1$ are the same or different organic groups, preferably substituted or unsubstituted aliphatic or aryl groups as defined by definition 5.

The invention includes methods for reacting organic alkali metallides having the formula YM, in which Y is any organic group and M is any alkali metal with a silane having the Formula (I) or Formula (II) wherein the product is a compound having the Formula (III) or Formula (IV).

A first step of such methods includes preparation of an organic alkali metallide. Methods for the preparation of such compounds are known. For example, any compound having a —CH group, preferably acidic, is reacted with an alkali metal alkyl having the formula $R^3M$, in which $R^3$ may be any hydrocarbyl group and M may be lithium, potassium or sodium. M may also be a magnesium halide. N-butyl lithium or tert-butyl lithium are preferred RM compounds. The reaction is conducted in a non-interfering solvent, preferably diethyl ether or tetrahydrofuran, which may also include or be combined or mixed with a hydrocarbon such as toluene. The reaction mixture contains a desired alkali metallide.

In a second step, the alkali metallide product of the first step is optionally but not necessarily isolated from the first step reaction mixture and reacted with a silane having the Formula (I) or the Formula (II). Methods for such isolating such compounds are known.

In one aspect of the invention, the compound having —CH group is a $C_5$-ring containing compound useful as an olefin polymerization catalyst ligand or as a precursor of such a ligand. Such ligands include but are not limited to substituted, unsubstituted, mono-, or bis- cyclopentadienyl, indenyl, naphthenyl and antracenyl ligands. These ligands may be hydrogenated. For example, such ligands include cyclopentadienes, bis-cyclopentadienes, indenes, bis-indenes, mono- and poly- alkyl, preferably methyl, substituted cyclopentadienes and indenes, such as tetraethyl cyclopentadiene and 2-methyl indene, 2-methyl-benzo(indene), bis-2-methyl-benzo(indene), dimethyl silane, substituted, unsubstituted and bis-phenanthrene, and cyclopentaphenanthrene which may be but need not be hydrogenated.

Another aspect of the invention may include a method which comprises combining a compound having the formula $Q^1$-(Z)-$Q^2Li_2$ and a compound having the formula $R^1_3SiO_3R^2$ in a non-interfering solvent wherein said compound having the formula $Q^1$-(Z)-$Q^2$Li reacts with the compound having the formula $R^1_3SiO_3R^2$ to produce a compound having the formula

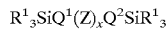

or

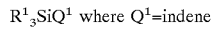

or

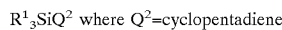

wherein $R^1$ and $Q^1$ and $Q^2$ each have 1 to 10 carbon atoms are the same or different aryl, preferably phenyl, and $R^2$ are identical or different alkyl groups.

Specifically, $Q^1$ and $Q^2$ (i) may be the same or different;
(ii) are preferably unsubstituted;
(iii) may be substituted at any position not occupied by linkage to $(Z)_x$ or to lithium and
(iv) Z is a linking group, preferably $(CH_2)_y$ in which y is 1 to 6 or $Si(R^2)$ wherein $R^2$ is a 1 to 6 carbon atom alkyl group.

Useful $Q^1$ and $Q^2$ substituents include one to six carbon atom alkyl, preferably methyl, groups; halogens, preferably chorine, fluorine or bromine, and substituents which form rings with two $Q^1$ or $Q^2$ carbon atoms.

Compounds having the formula $Q^1(Z) Q^2Li$ are prepared in known manner by reacting a compound of formula $Q^1(Z)_x Q^2$ with an alkyl lithium compound, preferably n-butyl or t-butyl lithium in a non-interfering solvent, preferably ether or tetrahydrofuran. The lithiation reaction is appropriately conducted at a temperature of from about –80° C. to about 40° C.

The reaction mixture which contains lithiated $Q^1$-$(X)_x Q^2$ may be combined directly with $R^1_3SiO_3SR^2$ to yield $R^1_3SiQ^1(X)_x Q^2SiR_3$. The reaction proceeds to substantial completion in about thirty minutes at room temperature. See Example 8. Alternatively, the lithium salt may be isolated prior to reaction with $R^1_3SiO_3SR^2$.

DETAILED DESCRIPTION OF THE INVENTION

The Formula (I) silanes may be prepared by reacting a compound of the formula $R^1SO_3H$, in which $R^1$ is any straight or branched chain alkyl group preferably having one to eight carbon atoms, with a compound of the formula $X_2SiQ_2$, in which X and Q are as defined.

The synthesis of one Formula (I) silane is illustrated by Equation 1:

(1)

RT=Room Temperature.

The novel Formula (II) silanes are synthesized by reacting $RSO_3H$ with a compound having the formula $(YNH)_2SiQ_2$, in which R and Q are as defined, and Y is an alkyl group which may be the same as or different from Q. See Equation 2:

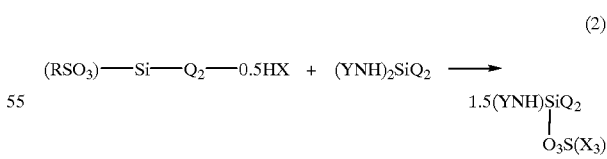

(2)

EXAMPLE 1

Preparation of Formula I Silane—$(MsO)_2SiMe_2 \cdot 0.5$ HCl $[(CH_3O_3S)_2Si(CH_3)_2 \cdot 0.5$ HCl]. To a 500 mL flask containing neat $Cl_2SiMe_2$ (64 g., 0.50 mol) was added MsOH (97 g., 1.01 mol); the immiscible solution rapidly evolved HCl that was scrubbed with NaOH (250 g., 50 wt % solution) or with iced water. After the solution was stirred overnight, the homogeneous oil was sparged with $N_2$ gas an additional day. This synthesis is illustrated by Equation 3:

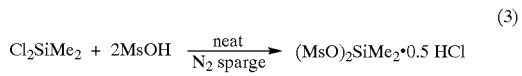
(3)

$^1$H NMR analysis of the product showed that one equivalent of HCl was present with two equivalents $(MsO)_2SiMe_2$; yield is quantitative.

EXAMPLE 2
Preparation of a Formula (II)

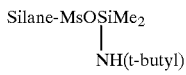

(a) Preparation of $(t-BuNH)_2SiMe_2$ (equation 4).

A 12 L flask equipped with an additional funnel and reflux condenser was charged with $t-BuNH_2$ (11 mol, 805 g) and THF (7 L). The solution was slowly treated with $Cl_2SiMe_2$ (5 mol, 645 g) that resulted in an exothermic reaction. After the temperature had dropped to 40° C., the white slurry was filtered, the $t-BuNH_3Cl$ was washed with THF (1 L), and the filtrate was reduced to an oil that contained 97% pure $(t-BuNH)_2SiMe2$ ($^1$H NMR). Yield was quantitative (1 Kg). See equation 4.

(4)

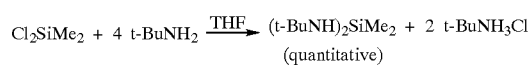

(b) Preparation of

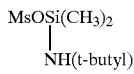

The $(t-BuNH)_2SiMe_2$ prepared as described in Example 2(a) was added to one equivalent of neat $(MsO)_2SiMe_2 \cdot 0.5$ HCl at room temperature, resulting in a 50–60° C. exotherm. The resulting oil which contained insoluble solids was filtered through a glass frit to give >98% pure $(t-BuNH)(MsO)SiMe_2$($^1$NMR). See equation 5.

(5)

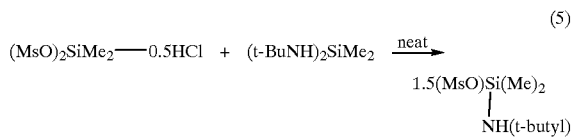

EXAMPLE 3
Formula (II) Silane—

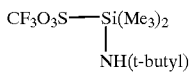

was prepared as described in Example 2 (Equation 5) except that $(TfO)_2Si(Me)_2$ replaces $(MsO)_2SiMe_2 \cdot 0.5$ HCl.

EXAMPLE 4
Preparation of 2-Methylcyclopentadienyl(t-Butylamido) Dimethylsilane (Equation 6). A 1 L flask was charged with 2-methylcyclopentadiene (16 g, 200 mmol) and THF (160 g). The solution was cooled (−10° C.) and treated with n-BuLi (1.6 M, 125 ML, 200 mmol). After the resulting white heterogeneous solution was stirred at room temperature for thirty minutes, the solution was treated with $(t-BuNH)(MsO)SiMe_2$ (47 g, 190 mmol) and the solution was stirred overnight. The solution was filtered through Celite, the residual LiOMs was washed with ether (500 mL), and the filtrate was reduced to an oil. No further purification was necessary. Yield was quantitative.

(6)

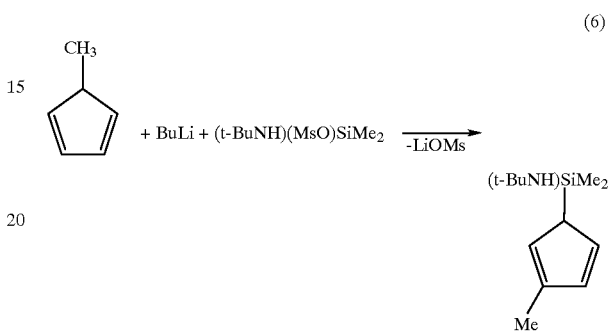

In this example, 2-methylcyclopentadiene may be replaced by cyclopentadiene to provide a quantitative yield of cyclopentadienyl (t-butyl amido) dimethylsilane.

Also in this example, 2-methylcyclopentadiene may be replaced by 3-methyl-2-ethyl-cyclopentadiene to provide a quantitative yield of 3-methyl-2-ethyl-cyclopentadienyl (t-butyl amido) dimethylsilane.

Also in this example, $t-BuNH(TfO)Si(Me)_2$ may be used with similar results.

This example illustrates a method in which a type II silane is added directly to the reaction mixture in which an alkali metallide is formed. Alternatively, the alkali metallide, here lithium-2-methylcyclopentadiene, may be isolated from the reaction mixture in known manner and thereafter reacted with either a type I or type II silane.

EXAMPLE 5

Preparation of 2-Methylindenyl(t-Butylamido) Dimethylsilane (Equation 7). A 5 L flask was charged with 2-methylindene (1.67 mol, 217 g) and ether (1.5 L). The solution was cooled (−10° C.) and treated with BuLi (1.67 mol, 1.04L). After the solution was stirred for one hour at room temperature, the solution was cooled (−10° C.) and $Me_2Si(MsO)NH(t-Bu)$ (a type II silane) was added in one portion, resulting in a 20° C. exotherm. After one hour at room temperature, the solution was filtered through Celite, the residual solid LiOMs was washed with ether (1.5 L), and the filtrate was reduced to a yellow oil that contained >98% pure 2-methylindenyl(t-butylamido) dimethylsilane ($^1$H NMR) in quantitative yield.

(7)

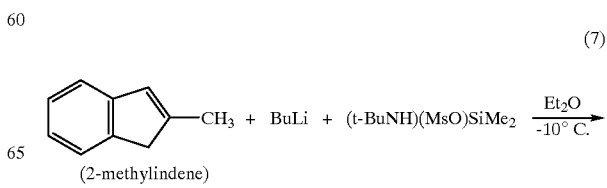

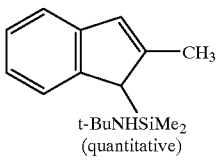

t-BuNHSiMe$_2$
(quantitative)

In this example, (t-BuNH)TfOSiMe$_2$ may be used instead of t-BuNH (MsO) SiMe$_2$.

Also, in this example, 2-methylindene may be replaced with fluorene to provide a quantitative yield of 9-fluorenyl-t-butylamido dimethylsilane.

Also, in this example, 2-methylindene may be replaced with bromobenzene to obtain a quantitative yield of the expected phenyl-t-butylamido dimethylsilane.

EXAMPLE 6

Preparation of bis(2-methyl-4,5-benzoindenyl) dimethylsilane (equation 8). A 2L flask charged with 2-methyl-4,5-benzo(indene) (73 g, 405 mmol) and ether (500 mL) was cooled to −10° C. and treated with n-BuLi (1.6 M, 255 mL, 405 mmol). The solution was allowed to warm to room temperature for 30 minutes, cooled to about −10° C., and then treated with a neat Formula I silane (MsO)$_2$SiMe$_2$.0.5 HCl (54 g, 203 mmol) resulting in a 10-15° C. exotherm. After one hour at room temperature, the white slurry was treated with CH$_2$Cl$_2$ (500 mL), and the solution was filtered through Celite into a 5L flask. The solids were washed with CH$_2$Cl$_2$ (500 mL), and the filtrate was evacuated to dryness. The white solid residue was treated with ether (200 mL), and the solvent was evacuated so that most of the residual CH$_2$Cl$_2$ was removed. The solid was then treated with ether (1 L) and triturated for thirty minutes before filtering and washing the white solid with ether (200 mL). Yields vary from 20-50%. The 2-methyl-4,5-benzo(indene) was recovered by treatment of the filtrate with NaOH (20 wt %) in THF.

(8)

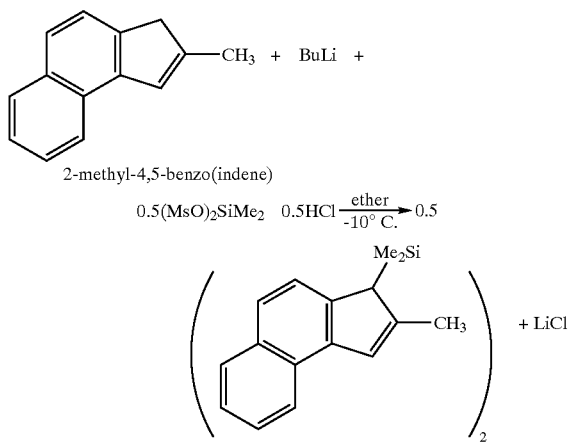

The above procedure was repeated, except that (MsO)$_2$SiMe$_2$.0.5HCl was replaced with (TfO)$_2$Si(Me)$_2$. The yield of bis(2-methyl-4,5-benzoindenyl) dimethylsilane was 60-65%.

EXAMPLE 7

Preparation of Metallocene Catalyst from the Example 5 Product (Equation 9). A 1 L flask was charged with bis(2-methyl-4,5-benzoindenyl) dimethylsilane (48 g, 115 mmol), toluene (480 mL), and ether (20 g, 270 mmol). The solution was cooled (−10° C.) and then treated with BuLi (1.6 M, 145 mL, 230 mmol). After the tanned-colored heterogeneous solution was stirred at room temperature for two hours, the solution was cooled (−20° C.) and treated with ZrCl$_4$ (27 g, 115 mmol). By the time the solution had warmed to −10° C., a bright yellow solution had resulted. After the yellow solution was stirred at room temperature for 2 hours, the solution was filtered, and the yellow solid was washed with toluene until the filtrate was pale yellow. The yellow filter cake was treated with an equal mass of Celite, the solids were slurried in dry CH$_2$Cl$_2$, and the product was extracted with CH$_2$Cl$_2$ through a layer of Celite into a 12 L flask that contained toluene (1 L); the extraction was stopped when the yellow color of the filtrate had turned translucent. The CH$_2$Cl$_2$ solvent was evaporated to give a toluene-slurry of yellow crystals. The solution was filtered, the yellow crystals were washed with toluene (1 L), and the yellow solid was slurried in toluene (5 L) for four hours. The solution was filtered to give 28 grams of diastereomerically pure metallocene ($^1$H NMR; yield—38%).

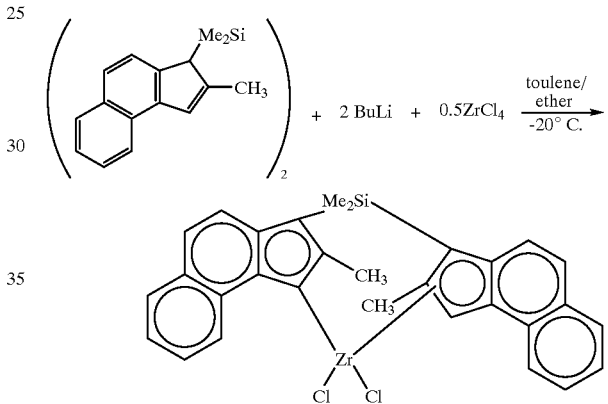

EXAMPLE 8

Preparation of Bis(3-Trimethylsilyl (TMS) indenyl) ethane (Equation 10). A 1L flask was charged with ethylene bis-indene (EBI) (0.100 mol, 26 g) and THF (260 g). The solution was cooled (−10° C.) and treated with BuLi (0.200 mol. 125 mL). After one hour at RT, the solution was cooled (−10° C.) and treated with Me$_3$Si(OMS) (0.200 mol., 34 g) in one portion. After thirty minutes at RT, the solution was filtered through Celite, the solids containing rac/meso bis (TMS) EBI were washed with THF (130 g), and the filtrate was reduced giving a solid that contained 98% rac-meso product in >98% yield. The product was extracted with heptane to separate the rac and meso isomers.

This procedure is illustrated by the following equation 10:

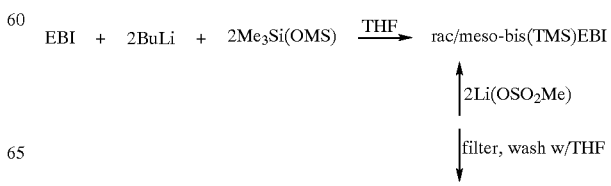

9

-continued

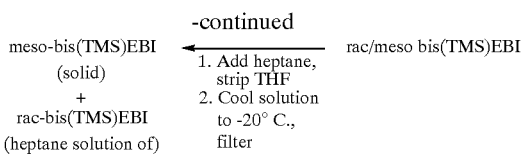

The above procedure was repeated with several analogs of EBI with similar results. Specific analogs of EBI were bis(2-methylindenyl) ethane, bis(4,7-dimethylindenyl) ethane, cyclopentadiene and methylcyclopentadiene. In this example, Me$_3$Si(OTf) may be used instead of Me$_3$Si(OMs).

EXAMPLE 9

Preparation of N-Silylated Cyclopentaphenanthrene. This procedure is illustrated by equation 11:

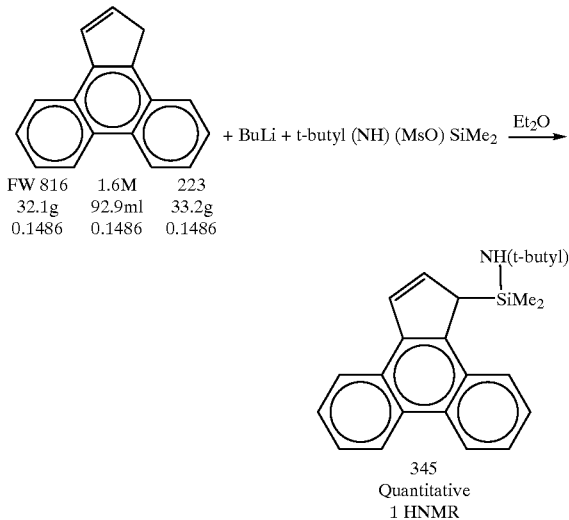

FW 816    1.6M    223
32.1g    92.9ml    33.2g
0.1486   0.1486   0.1486

345
Quantitative
1 HNMR

10

Cyclopentaphenanthrene is mostly dissolved in diethyl ether (800 mL), n-BuLi is added, and the reaction mixture was stirred overnight.

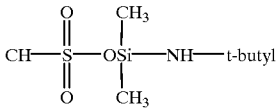

was added neat, followed by stirring for one-half hour. The reaction mixture was filtered. Ether was removed. Yield— quantitative. In this reaction, any compound of Formula (II), page 5, may be used instead of t-butyl NHMsOSiMe$_2$. Compounds obtaining the corresponding R groups instead of t-butyl are produced.

In this example, CF$_3$SO$_3$Si(CH$_3$)$_2$NH t-butyl may be used instead of CH$_3$SO$_3$SI(CH$_3$)$_2$NH t-butyl.

I claim:

1. A method for preparing an N-silylated mono- or bis- cyclopentadienyl or indenyl compound which comprises reacting a lithiated mono- or bis- cyclopentadienyl or indenyl compound with a compound of the formula:

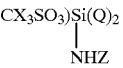

in which X is H or F, Q is an alkyl or aryl hydrocarbyl group, and Z is an alkyl or aryl hydrocarbyl group which may be the same as or different from Q.

2. A method for preparing an N-silylated mono- or bis- cyclopentadienyl or indenyl compound which comprises reacting a lithiated mono- or bis- cyclopentadienyl or indenyl compound with the compound

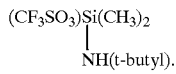

* * * * *